United States Patent
Abernethy et al.

(10) Patent No.: US 8,587,438 B2
(45) Date of Patent: Nov. 19, 2013

(54) SYSTEM AND METHOD FOR DETECTING ACTIVITIES OF DAILY LIVING OF A PERSON

(75) Inventors: Simon George Abernethy, Eindhoven (NL); Alexander Sinitsyn, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 399 days.

(21) Appl. No.: 12/991,923

(22) PCT Filed: May 6, 2009

(86) PCT No.: PCT/IB2009/051853
§ 371 (c)(1),
(2), (4) Date: Nov. 10, 2010

(87) PCT Pub. No.: WO2009/138905
PCT Pub. Date: Nov. 19, 2009

(65) Prior Publication Data
US 2011/0068931 A1 Mar. 24, 2011

(30) Foreign Application Priority Data
May 13, 2008 (EP) .................................. 08156093

(51) Int. Cl.
G08B 23/00 (2006.01)
(52) U.S. Cl.
USPC .................................. 340/573.1; 340/573.4
(58) Field of Classification Search
USPC ................. 340/573.1, 573.4, 568.2; 702/188
See application file for complete search history.

(56) References Cited

U.S. PATENT DOCUMENTS

| | | | |
|---|---|---|---|
| 5,515,858 A * | 5/1996 | Myllymaki | 600/301 |
| 6,002,994 A | 12/1999 | Lane et al. | |
| 7,953,571 B2 * | 5/2011 | Odaka et al. | 702/188 |
| 2005/0184870 A1 | 8/2005 | Galperin et al. | |
| 2007/0069900 A1 | 3/2007 | Stern et al. | |
| 2010/0201573 A1 * | 8/2010 | Lamming | 342/451 |

FOREIGN PATENT DOCUMENTS

WO 9316636 A1 9/1993

OTHER PUBLICATIONS

Amft et al: "Probabilistic Parsing of Dietary Activity Events"; Wearable Computing Lab, Eth Zurich, Switzerland, 4th International Workshop on Wearable and Implantable Body Sensor Networks (BSN 2007), IFMBE Proceedings, 2007, vol. 13, 6th Session, pp. 242-247.
International Search Report—PCT/IB2009/051853, Dec. 8, 2009.

* cited by examiner

Primary Examiner — John A Tweel, Jr.

(57) ABSTRACT

The system according to the invention comprises a plurality of sensors (10), (20) arranged to measure an ambient condition of a person. A movement of the person is being detected by the movement sensor (20) included in the system. The system further comprises interpretation means (110) arranged for interpreting a plurality of first output signals (100) and a second output signal (200). The plurality of first output signals (100) is provided by the ambient sensors (10) and the second output signal (200) is provided by the movement sensor (20). The interpretation means (110) are further arranged to determine an activity of daily living of said person. The interpretation means may provide an alarm signal (120) indicating that the person may need direct assistance and a warning signal (130) indicating a potential deteriorating health condition of the person.

13 Claims, 5 Drawing Sheets

SYSTEM AND METHOD FOR DETECTING ACTIVITIES OF DAILY LIVING OF A PERSON

FIELD OF THE INVENTION

This invention relates to a system and method for detecting activities of daily living of a person.

BACKGROUND OF THE INVENTION

Current demographics show a rise in the number of seniors. There is further a trend that these seniors want to stay living independently in their own home. For their children this can become a worry, and especially when children do not live close to their parents it is difficult for them to monitor their wellbeing. There is therefore a need for a system that assists these remote living children to monitor the well being of their parents while maintaining the privacy of said parents.

US20070069900A1 discloses a system and method for monitoring one or more humans while maintaining the privacy of those individuals. The system includes one or more activity pickups that create one or more information outputs. A computer system monitors one or more of the information outputs and processes the information outputs to determine when one or more types of inactivity of the human in an area exceeds one or more threshold of inactivity. Alarms and/or indications activate when one or more of the thresholds of inactivity is exceeded. Various types of thresholds of inactivity are disclosed.

A disadvantage is that the information provided by the system is limited to potential hazardous situations that are characterized by an amount of a type of inactivity that has been taken place over time.

SUMMARY OF THE INVENTION

It is therefore an object of the invention to provide a system for non intrusive monitoring of a person that provides more information on the person being monitored.

The object is achieved with a system for non intrusive monitoring of a person that comprises at least one ambient sensor arranged for measuring an ambient condition of said person, a movement sensor arranged for detecting a movement of said person and interpretation means arranged for interpreting a first output signal provided by the at least one ambient sensor and a second output signal provided by the movement sensor to determine an activity of daily living of said person.

The invention is based on the insight that for the person being monitored the absence of a camera will make the monitoring acceptable. Non intrusive monitoring may be realized with relative simple sensors that provide data on specific ambient conditions, such as for example temperature or humidity, and a movement sensor. These simple sensors are considered as less privacy intruding and therefore more easily accepted. On the other hand with the data provided by these sensors activities of daily living may be determined and provide more information on the person being monitored. Activities of daily living concern basic activities that a person executes on a regular basis. Examples of activities of daily living are bathing, dressing, eating, toilet use, etc. The system that uses the at least one ambient sensor and the movement sensor thus provides information on the activity of the person in a non intrusive way, thereby achieving the object of the invention.

A further advantage of the system is that these sensors for measuring an ambient condition are cheap compared to a camera. Also a movement sensor is a cheap component. An example of a movement sensor is a PIR (Passive Infra Red) sensor.

For example with a humidity sensor and a movement sensor in the bathroom it may be determined that the person is taking a shower. In a further example with a temperature sensor and a movement sensor in the kitchen it may be determined that the person is preparing a hot meal. It is a further advantage that the ambient sensor for measuring an ambient condition and the movement sensor may be stationary sensors that are located for example in the bathroom and in the kitchen. This makes it unnecessary for the person to wear a device.

In a further embodiment the interpretation means are arranged for providing a timestamp to the first output signal of the at least one ambient sensor in dependence of a detected movement as indicated by the second output signal. In yet a further embodiment interpretation means are further arranged for calculating a time difference between two timestamps. By adding time information to the measured ambient condition the time spent that an activity takes place may be determined. In a further embodiment the interpretation means are arranged to determine the activity in dependence of a comparison of the first output signal with a threshold. For example to determine whether the activity is 'taking a hot shower' the humidity condition in the bathroom must pass a threshold.

In a further embodiment the interpretation means are arranged to determine the activity of daily living in dependence of a comparison of the first output signal with a threshold and are the interpretation means further arranged for generating an alarm signal dependent on the determined activity of said person and the time difference. This provides the advantage that for example an alarm may be given if the person stays too long in the bathroom with the hot shower running indicating that for example the person has become unwell in the bathroom.

In a further embodiment of the system the interpretation means are further arranged to store the determined activity of said person in an activity profile of said person. This provides the advantage that the behavioral pattern of activities of the person is stored. Shifts in this pattern may indicate that the person is in need of help. For example the person may start forgetting to take a regular shower. Or in a further example the person is taking less frequently a hot meal because he is feeling depressed.

In a further embodiment the interpretation means are further arranged to detect an irregularity in the activity profile. By adding time information to the measured ambient condition the time spent between the activities may be determined. With the time information the frequency of the activity may be determined. For example the frequency of the determined activity 'preparing a hot meal' may be 'once a day', or '5 times a week'. An irregularity in the activity profile may for example be that the time spent between the determined activities of 'preparing a hot meal' has increased. For example the average time spent may be determined using the data from the activity profile. When the time spent between two successive determined activities of 'preparing a hot meal' is larger than for example 1.5 times the average time spent this indicates an irregularity.

In a further embodiment the interpretation means are further arranged for generating a warning signal in response to the detected irregularity. The irregularity may indicate that the person is in need of help. In a further example a family member or close relative may be advised by the system (using the warning signal) to pay a visit to the person.

In a further embodiment the warning signal is given to the person himself. In this embodiment the warning signal is a feedback signal advising the person for example to take a shower.

The invention further provides a method for non intrusive monitoring of a person characterized in comprising the steps of measuring an ambient condition of said person
detecting a movement of said person;
interpreting said measured ambient condition and said movement to determine an activity of daily living of said person The non intrusive character of the monitoring is in the method realized by measuring at least one ambient condition of the person rather than by for example surveillance by camera of the person. Further the movement of the person is detected with for example a PIR sensor. Movement sensors are for example used to switch on lighting and people are familiar with their usage. Therefore monitoring by measuring one or more ambient conditions of the person and by detecting the movement of said person will be experienced as non intrusive.

In a further embodiment of the method the determined activity of said person is time-stamped and stored in an activity profile. The stored activities of the person form a behavioral pattern that characterizes said person. Deviations in the monitored activities of the person may be used as an indicator of the well-being of the person. For example elderly people that start suffering from dementia will show shifts in their behavioral pattern. They will start to forget to take a shower and lose the feeling of time. Therefore in a further embodiment of the method the activity profile of the person is analyzed for irregularities or shifts in the behavioral patterns.

BRIEF DESCRIPTION OF THE DRAWINGS

The invention will now be described, by way of example only, with reference to the following drawings, in which.

DETAILED DESCRIPTION OF THE EMBODIMENTS

Figure 1:
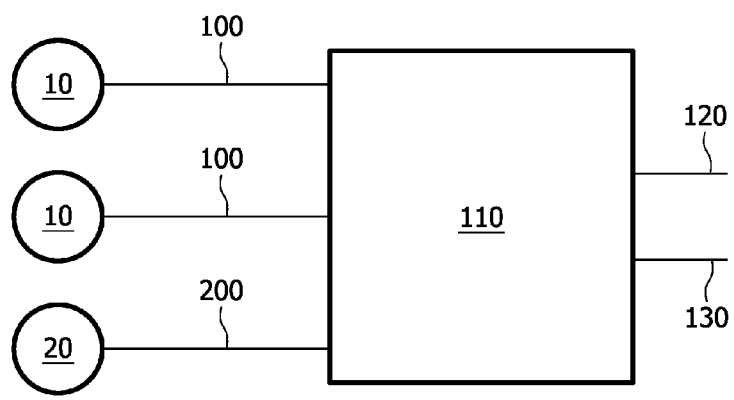
FIG. 1 shows an embodiment of the system according to the invention.

FIG. 1 shows an embodiment of the system according to the invention comprising a plurality of sensors 10, 20 arranged to measure an ambient condition of a person. A movement of the person that is monitored is being detected by the movement sensor 20 included in the system. The system further comprises interpretation means 110 arranged for interpreting a plurality of first output signals 100 and a second output signal 200. The plurality of first output signals 100 is provided by the ambient sensors 10 and the second output signal 200 is provided by the movement sensor 20. The interpretation means 110 are further arranged to determine an activity of daily living of said person. The interpretation means may provide an alarm signal 120 indicating that the person may need direct assistance and a warning signal 130 indicating a potential deteriorating health condition of the person.

In a further embodiment the system may comprise a plurality of movement sensors 20 providing a plurality of second output signals 200. For example the home of the person being monitored may comprise two or more rooms, each one of these rooms comprising at least one movement sensor.

Figure 2:
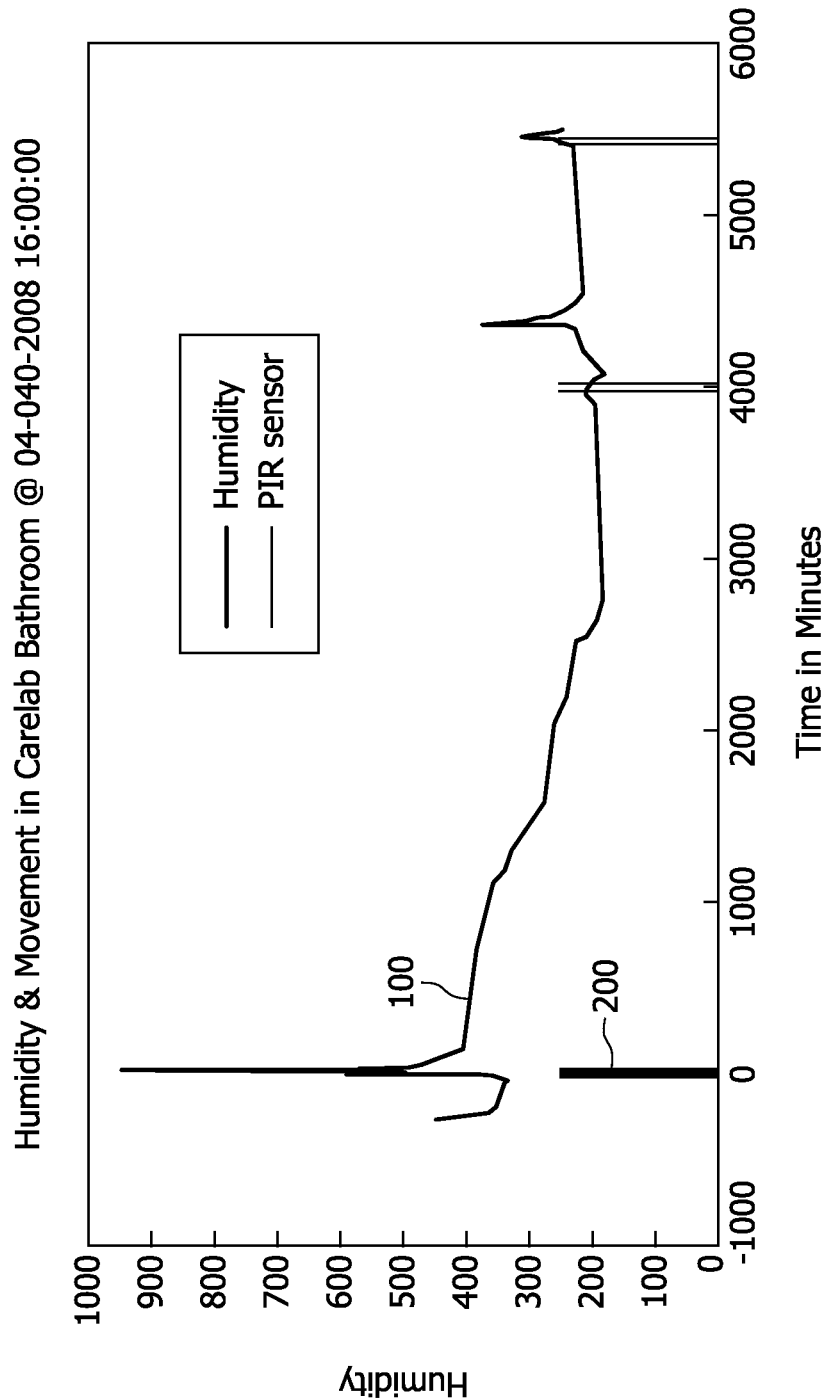
FIG. 2 shows a graph with a first output signal and a second output signal.

FIG. 2 shows a first output signal 100 provided by a humidity sensor 10 and a second output signal 200 provided by a movement sensor 20 over a time of approximately 4 days. The movement sensor is realized by a Passive IR (PIR) detector that is focused on the shower area. The humidity sensor is mounted in the bathroom near the shower. In the graph of FIG. 2 three peaks of various sizes are observed indicating shower usage of different length using water of different temperatures (e.g. hot and cold shower). Next to the three peaks that characterize fast changes in humidity also a slow change in humidity is seen; this slow change is caused by the changing weather conditions and air-conditioning systems that were operating in the room where the measurements shown in the graph of FIG. 2 were made.

Figure 3:
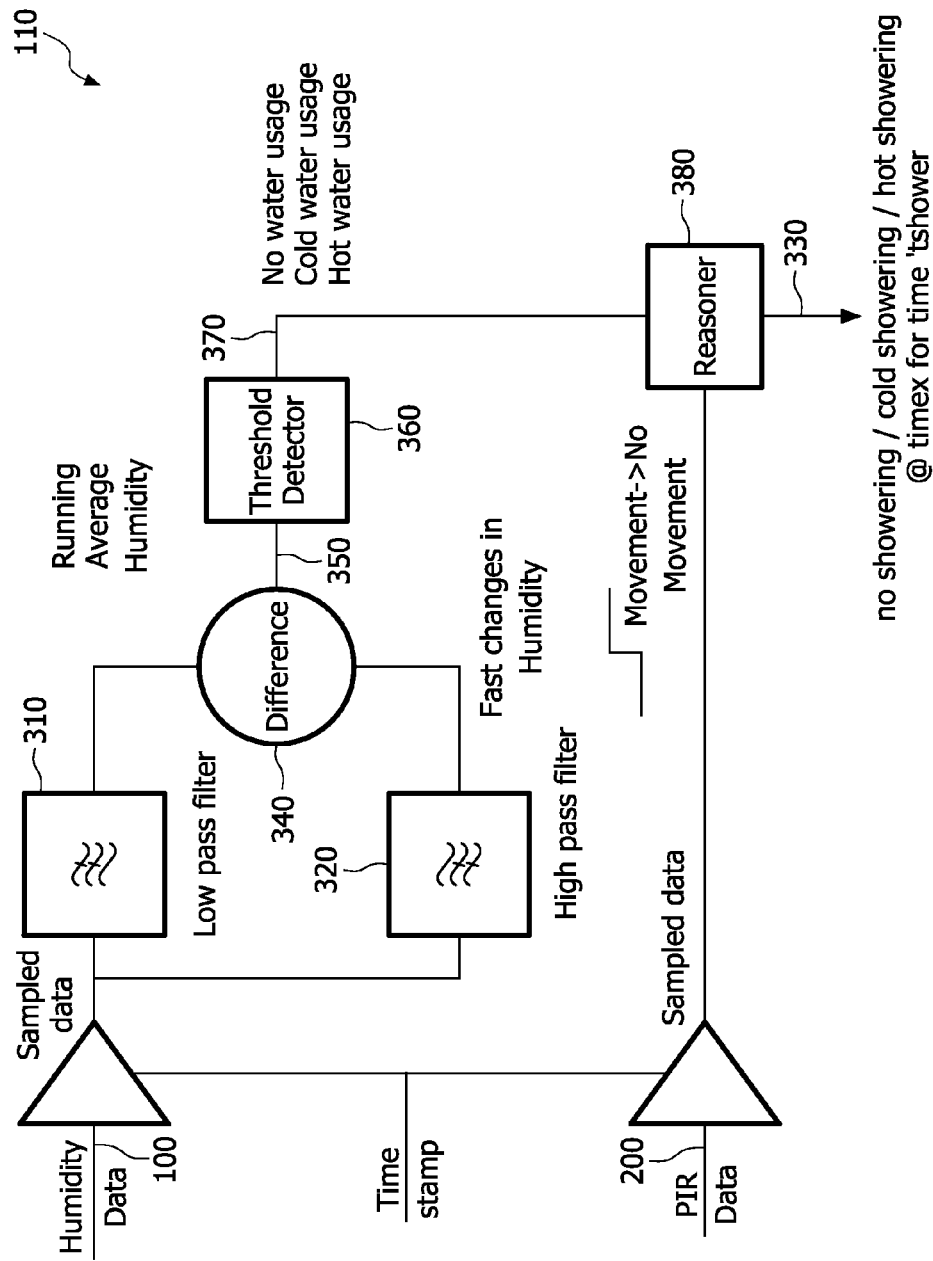
FIG. 3 shows a further embodiment of the system according the invention.

FIG. 3 shows an embodiment of the interpretation means 110 in the system according to the invention. The interpretation means are arranged to interpret the first and second output signal 100, 200 and to provide output data 330 on the activity of daily living of the person. The first output signal 100 and the second output signal 200 are sampled and timestamped. With timestamped is meant that time information is added to the sampled first output signal. This time information may also comprise data information. The timestamp is generated when a movement is detected as indicated by a change in the second output signal 200. In a further embodiment with time stamping the time information is also added to the second output signal. The system further comprises filter means 310, 320. With a low pass filter 310 the average value of the sampled humidity signal is determined. With the high pass filter 320 the fast changes in the humidity are taken out of the sampled humidity signal. The difference 340 between the output of the high pass filter and the low pass filter provides data 350 on fast changes in the humidity compensated for slow changes caused by air conditioning or changing weather conditions. Said data 350 on fast changes provides therefore information on changes in humidity caused by actual water usage of the person. Said data 350 on fast changes is compared with three humidity levels in the module referred to as threshold detector 360 to provide a third output signal 370 indicating whether no water is used, cold water is used or hot water is used. By combining the third output signal 370 with the sampled second output signal of the PIR detector the module referred to as Reasoner 380 provides information on whether the person has taken a hot shower, a cold shower or no shower at all.

Using the timestamps and collecting the information provided by the Reasoner 380 in a personal profile the output data 330 of the interpretation means may further comprise data on the periods of cleansing, the regularity on these periods, Hot/Cold water usage. The output data 330 may further comprise data on periods of inactivity in the shower with no exit which may indicate a potential hazardous situation such as a fall. By collating the information provided by the Reasoner 380 over time the pattern/regularity of cleansing of the person may be monitored.

Figure 4:
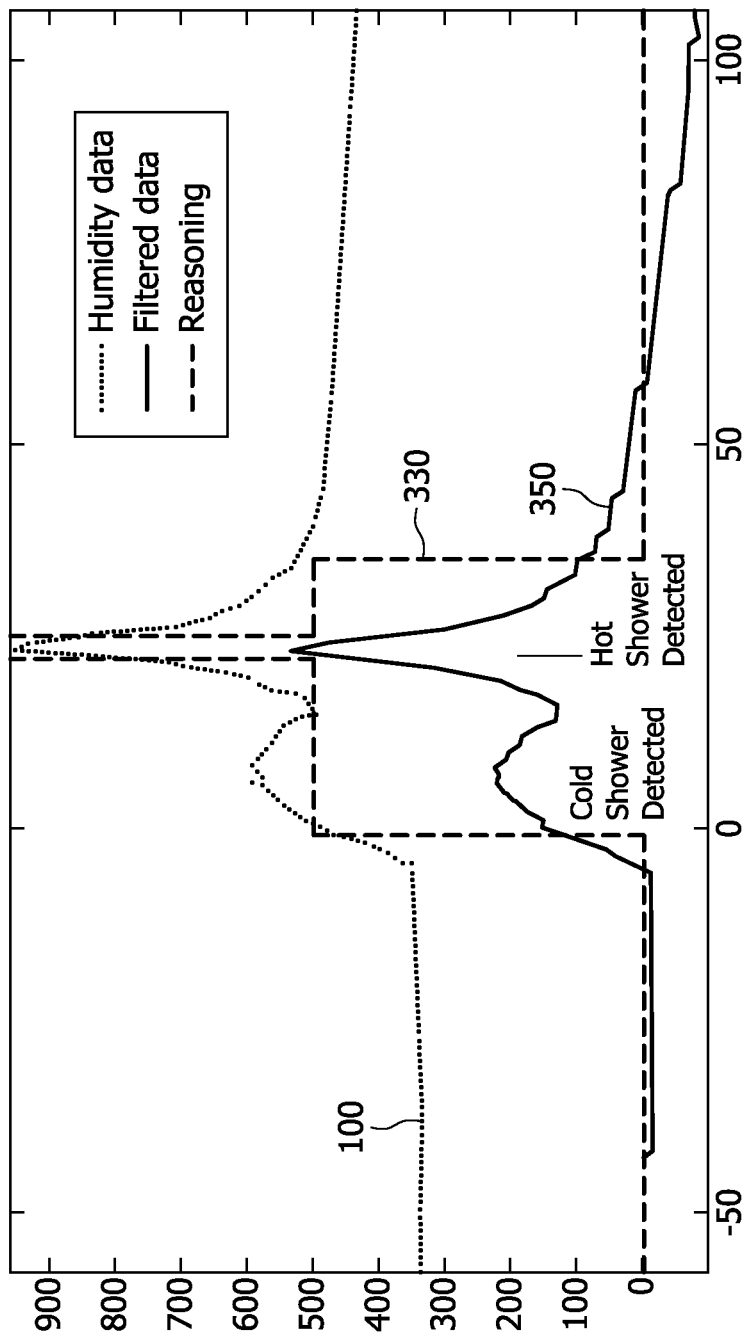
FIG. 4 shows a graph with signals in the system of FIG. 3.

FIG. 4 shows a graph with the first output signal 100 of the humidity sensor. FIG. 4 further shows the data 350 on fast changes in the humidity compensated for slow changes caused by air conditioning or changing weather conditions and said data provides therefore information on changes in humidity caused by actual water usage of the person. FIG. 4 further shows the output data 330 of the interpretation means providing data on the activity of daily living of the person.

Figure 5:
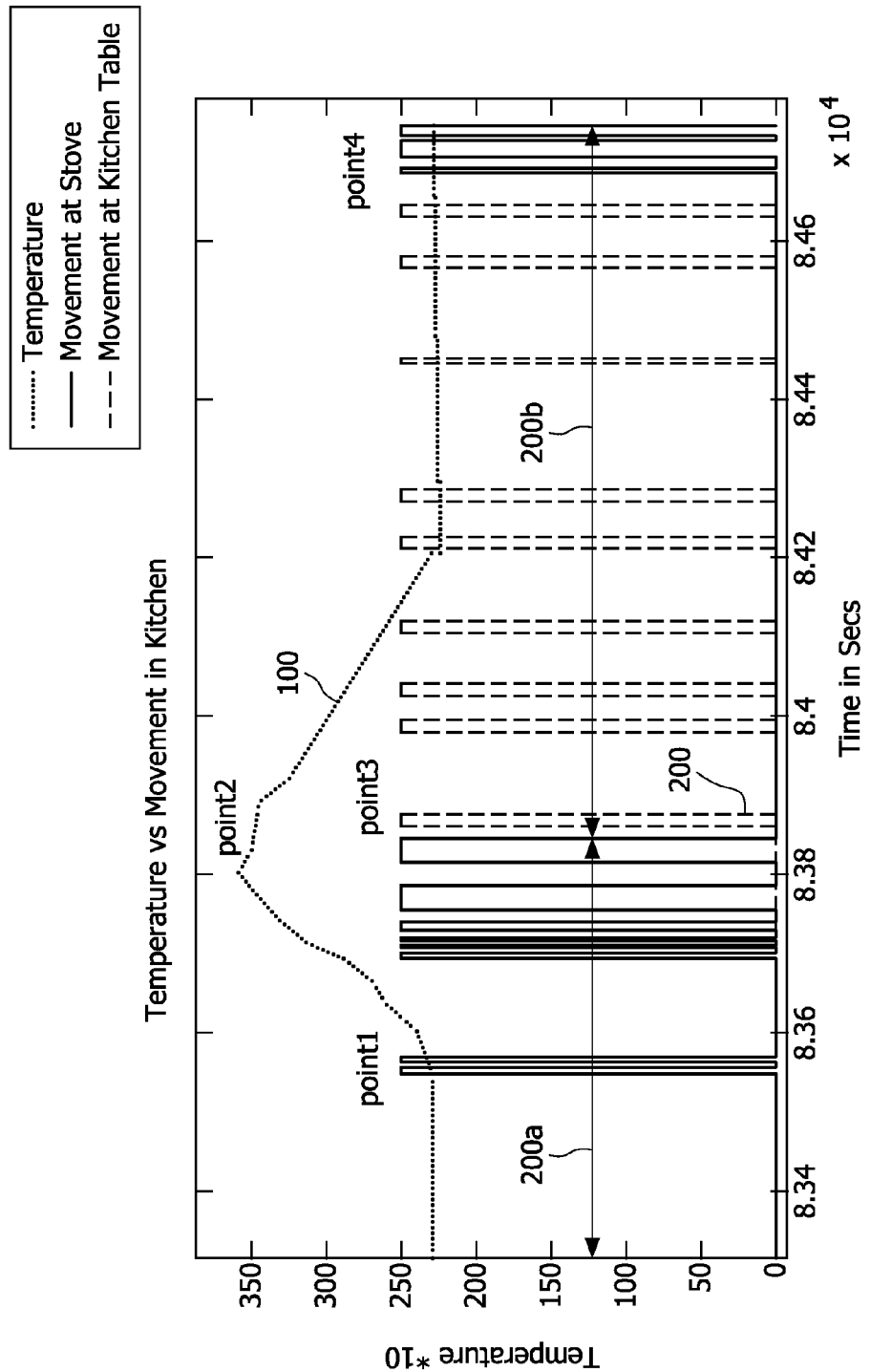
FIG. 5 shows a further graph with a first output signal and a second output signal.

FIG. 5 shows output signals 100, 200 from sensors 10, 20 used in a further embodiment of the system. The first output signal 100 is provided by a temperature sensor. The second output signal comprises the output signals 200 of two movement sensors. A first movement sensor detects movements of the person in the vicinity of the stove (indicated by 200a), the second movement sensor detects movements of the person close to the kitchen table (indicated by 200b).

In FIG. 5 three points are identified. Point 1 indicates the movement of the person in the vicinity of the stove. Point 2 also indicates movement of the person in the vicinity of the stove accompanied by a temperature rise. Point 1 and 2 indicate the activity of the preparation of a hot meal. Point 3 indicates a drop in temperature coinciding with no movement registered in the area of the stove plus movement captured from the person close to the kitchen table. This indicates that the person sat down and is eating his hot meal.

By further careful interpretation of the output signals 100, 200 of the sensors 10, 20 the Reasoner 380 may provide output data 330 on: periods of cooking, regularity of the preparation of hot food on a stove, times that hot food preparation takes place, the probable consumption of food. By collating the data over time in a personal profile the pattern/regularity of hot food preparation and inferred consumption may be monitored.

In a further embodiment the interpretation means 110 may be implemented with a processing unit. The first and second output signal 100, 200 may be converted to the digital domain using an analogue to digital converter. The digital representation of the first and second output signal 100, 200 is further analyzed by the processing unit. The processing unit may add timing information to the digital representation of the first and second output signal upon detecting a change in the digital representation of the second output signal, said change resulting from a movement of the person. The interpretation means 110 may further comprise a memory storing code that is being used to interpret the digital representation of the first and second output signal is further analyzed by the processing unit. For example with the code the step of comparing of the measured ambient condition with a threshold may be programmed. The processing unit is arranged to execute the code. The result of the execution of the code provides data on the activity of the person. Said activity may be stored in the memory, together with the timing information for that activity, thereby creating an activity profile for that person. The activity profile may be consulted by a family member that provides said family member peace of mind as the pattern indicates that 'mum is doing well'. The system may for example have an internet access allowing the caregiver to access the memory comprising the personal profile. The caregiver may use the activity profile to determine the mental ability of the person.

The invention claimed is:

1. A system for non-intrusive monitoring of a person the system comprising:
    at least one ambient sensor arranged for measuring an ambient condition of said person;
    a movement sensor arranged for detecting a movement of said person;
    interpretation means arranged for:
        interpreting a first output signal provided by the at least one ambient sensor and a second output signal provided by the movement sensor to determine an activity of daily living of said person, and
        providing a timestamp to the first output signal of the at least one ambient sensor in dependence of a detected movement as indicated by the second output signal.

2. The system according to claim 1 wherein the interpretation means are further arranged for calculating a time difference between two timestamps.

3. The system according to claim 1 wherein the interpretation means are arranged to determine the activity in dependence of a comparison of the first output signal with a threshold.

4. The system according to claim 2 wherein the interpretation means are arranged to determine the activity in dependence of a comparison of the first output signal with a threshold and wherein the interpretation means are further arranged for generating an alarm signal dependent on the determined activity of said person and the time difference.

5. The system according to claim 1 wherein the determined activity of said person is taken from a group consisting of: eating, cooking, and washing.

6. The system according to claim 1, wherein the interpretation means are further arranged to store the determined activity of said person in an activity profile of said person.

7. The system according to claim 6 wherein the interpretation means are further arranged to detect an irregularity in the activity profile, and wherein the interpretation means are further arranged for generating a warning signal in response to the detected irregularity.

8. The system according to claim 7 wherein the interpretation means are arranged to determine a frequency of the activity in the activity profile, the detected irregularity being dependent on a change in the frequency.

9. The system according to claim 7 wherein the system is arranged to provide the generated warning signal to the person or a caregiver.

10. A method for non-intrusive monitoring of a person characterized in comprising the steps of
    measuring an ambient condition of said person
    detecting a movement of said person;
    interpreting said measured ambient condition and said movement to determine an activity of daily living of said person, wherein a time-stamp is provided to the measured ambient condition in dependence of the detected movement.

11. The method according to claim 10 wherein the step of interpreting said measured ambient condition and said movement comprises the steps of
    calculating a time difference between two timestamps;
    generating an alarm signal dependent on the determined activity of said person and the time difference.

12. The method according to claim 10 wherein the step of interpreting said measured ambient condition and said movement is further arranged to store the determined activity of said person in an activity profile of said person.

13. The method according to claim 12 wherein the step of interpreting said measured ambient condition and said movement further comprises the steps of
    detecting an irregularity in the activity profile;
    generating a warning signal in response to the detected irregularity.

* * * * *